United States Patent [19]

Goto et al.

[11] Patent Number: 5,180,746

[45] Date of Patent: Jan. 19, 1993

[54] ARALKYLAMINE COMPOUNDS

[75] Inventors: Giichi Goto, Toyono; Akinobu Nagaoka, Kawanishi; Yuji Ishihara, Itami, all of Japan

[73] Assignee: Takeda Chemical Industries, Ltd., Osaka, Japan

[21] Appl. No.: 480,564

[22] Filed: Feb. 15, 1990

[30] Foreign Application Priority Data

Feb. 17, 1989 [JP] Japan .................. 1-038999
Jul. 11, 1989 [JP] Japan .................. 1-179438

[51] Int. Cl.⁵ .................. A61K 31/125; C07C 211/27
[52] U.S. Cl. .................. 514/654; 514/648; 514/655; 514/429; 564/321; 564/378; 564/387; 548/577
[58] Field of Search ............... 564/321, 378, 387; 514/648, 654, 655

[56] References Cited

U.S. PATENT DOCUMENTS

| | | | |
|---|---|---|---|
| 2,541,967 | 2/1951 | Kolloff et al. | 260/570.5 |
| 2,549,685 | 4/1951 | Heinzelmann | 260/570.5 |
| 4,564,641 | 1/1986 | Seitz et al. | 514/650 |
| 4,847,254 | 7/1989 | Boegesoe et al. | 514/256 |
| 4,946,863 | 8/1990 | Boegesoe et al. | 564/387 X |

FOREIGN PATENT DOCUMENTS

| | | | |
|---|---|---|---|
| 76197 | 2/1988 | Australia . | |
| 78224 | 3/1988 | Australia . | |
| 82417 | 6/1988 | Australia . | |
| 20579 | 2/1989 | Australia . | |
| 365558 | 12/1977 | Austria . | |
| 456542 | 6/1944 | Belgium . | |
| 0110253 | 11/1983 | European Pat. Off. . | |
| 0229391 | 7/1987 | European Pat. Off. . | |
| 0281261 | 2/1988 | European Pat. Off. . | |
| 0259782 | 3/1988 | European Pat. Off. . | 564/378 |
| 0286278 | 3/1988 | European Pat. Off. . | |
| 0303961 | 8/1988 | European Pat. Off. . | |
| 0296560 | 12/1988 | European Pat. Off. . | |
| 0326106 | 8/1989 | European Pat. Off. . | |
| 514418 | 12/1930 | Fed. Rep. of Germany . | |
| 2339715 | 2/1975 | Fed. Rep. of Germany . | |
| 162281 | 1/1974 | New Zealand . | |
| 179078 | 4/1978 | New Zealand . | |
| 185162 | 3/1980 | New Zealand . | |
| 194329 | 5/1982 | New Zealand . | |
| 193236 | 9/1982 | New Zealand . | |
| 225758 | 10/1990 | New Zealand . | |
| 1076966 | 7/1967 | United Kingdom . | |
| 1507463 | 4/1978 | United Kingdom . | |
| 1597140 | 9/1981 | United Kingdom . | |

OTHER PUBLICATIONS

C.A. 111: 133804y (1989), vol. 111, Freedman, et al.
C.A. 110: 95584v (1989), vol. 110, Reenmann, et al.
C.A. 104: 148762m (1986), vol. 104, Nakao, et al.
C.A. 104: 148763n (1986), vol. 104, Nakao, et al.
C.A. 101: 110759r (1984), vol. 101, Nakao, et al.
C.A. 85: 159770c (1970), vol. 85, Hammar.
C.A. 74: 13005h(1971), vol. 74, Hansen.
C.A. 66: 65310h (1967), vol. 66, Seeboth, et al.

Primary Examiner—Joseph Paul Brust
Attorney, Agent, or Firm—Wegner, Cantor, Mueller & Player

[57] ABSTRACT

An aralkylamine compound of the formula

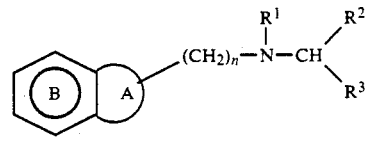

wherein $R^1$ means a hydrogen atom or a lower alkyl group; $R^2$ means an aromatic group which may be substituted; $R^3$ means a hydrogen atom, a lower alkyl group or an aromatic group which may be substituted; n means an integer of 0 to 7; ring A means a five-through eight-membered cyclic group which may be substituted and may contain one or two hetero atom(s) of O and S atoms as the ring-constituents; and ring B means a benzene ring which may be substituted, or a salt thereof, which is useful as an cholinesterase inhibitor and a cerebral function ameliorating agent.

7 Claims, No Drawings

ARALKYLAMINE COMPOUNDS

The present invention relates to novel aralkylamine derivatives and their salts, which are of value as medicaments and particularly as, brain, function ameliorating agents which may be indicated, for example in senile dementia and Alzheimer's disease and so on.

With the proportion of elderly people in the total population being on the steady increase, a number of compounds claimed to have brain function ameliorating activity have been introduced. Among such compounds, the cholinesterase inhibitor physostigmine has been found to possess a brain function ameliorating action.

Physostigmine, however, has several drawbacks, among which are a short duration of action and a high toxicity potential.

The present invention provides a novel compound which is more potent, longer-acting and less toxic than any compound hitherto known to have brain function improving activity.

Compounds are provided which are function ameliorating agents having anticholinesterase activity aralkylamine derivatives, which have the formula

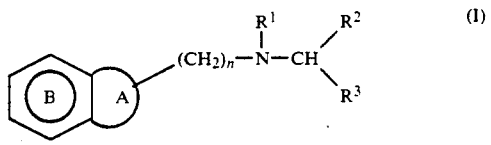

wherein $R^1$ means a hydrogen atom or a lower alkyl group; $R^2$ means an aromatic group which may be substituted; $R^3$ means a hydrogen atom, a lower alkyl group or an aromatic group which may be substituted; n means an integer of 0 to 7; ring A means a five-through eight-membered cyclic group which may be substituted and may contain one or two hetero atom(s) of O and S atoms as the ring-constituents; and ring B means a benzene ring which may be substituted, and physiologically acceptable salts thereof. The inventors further discovered that these compounds have excellent brain function ameliorating activity and accomplished the present invention.

The present invention is, therefore, directed to a compound of the formula (I) [hereinafter referred to sometimes as compound (I)]or a salt thereof, a process for production thereof, and a cholinesterase inhibitor composition and a brain function ameliorating composition each containing said compound or salt.

Referring to the above formula (I), the lower alkyl group, denoted by $R^1$ or $R^3$, includes $C_{1-6}$ alkyl groups (e.g. methyl, ethyl, n-propyl, i-propyl, n-butyl, i-butyl, t-butyl, n-pentyl, n-hexyl, etc.).

Referring, further, to the formula (I), the aromatic group of the "aromatic group which may be substituted", denoted by $R^2$ or $R^3$, include phenyl, naphthyl and so on.

The substituent groups which may substitute this aromatic group include, among others, $C_{1-4}$ alkyl (e.g. methyl, ethyl, propyl, butyl, etc.), halogens (e.g. chlorine, bromine, iodine, etc.), nitro, cyano, hydroxy, $C_{1-4}$ alkoxy (e.g. methoxy, ethoxy, propoxy, butyloxy, isopropoxy, etc.), $C_{1-4}$ alkylthio (e.g. methylthio, ethylthio, propylthio, isopropylthio, butylthio, etc.), amino, mono- or di-$C_{1-4}$ alkylamino (e.g. methylamino, ethylamino, propylamino, dimethylamino, diethylamino, etc.), $C_{1-4}$ alkylcarbonylamino (e.g. acetylamino, propionylamino, butyrylamino, etc.), $C_{1-4}$ alkylsulfonylamino (e.g. methylsulfonylamino, ethylsulfonylamino, propylsulfonylamino, etc.), $C_{1-4}$ alkoxycarbonyl (e.g. methoxycarbonyl, ethoxycarbonyl, propoxycarbonyl, isobutoxycarbonyl, etc.), hydroxycarbonyl, $C_{1-4}$ alkylcarbonyl (e.g. methylcarbonyl, ethylcarbonyl, butylcarbonyl, etc.), cyclohexylcarbonyl, carbamoyl, mono- or di-$C_{1-4}$ alkylcarbamoyl (e.g. methylcarbamoyl, ethylcarbamoyl, propylcarbamoyl, butylcarbamoyl, diethylcarbamoyl, dibutylcarbamoyl, etc.) and $C_{1-4}$-alkylsulfonyl (e.g. methylsulfonyl, ethylsulfonyl, propylsulfonyl, etc.), cyclopentylsulfonyl, cyclohexylsulfonyl, as well as phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino and phenylsulfonylamino, each of which may have 1 to 4 substituents. Here, the substituents on this phenyl or naphthyl ring include, among others, $C_{1-4}$ alkyl (e.g. methyl, ethyl, propyl, butyl, isopropyl, etc.), $C_{1-4}$ alkoxy (e.g. methoxy, ethoxy, n-propoxy, i-propoxy, n-butoxy, etc.), halogens (e.g. chlorine, bromine, iodine, etc.), hydroxy, benzoxy, amino, mono- or di-$C_{1-4}$ alkylamino, nitro and $C_{1-4}$ alkoxycarbonyl.

The preferred number of substituent groups substituting the aromatic group is about 1 to 3.

Referring, further, to the formula (I), ring B means a benzene ring which may be substituted. Here, the substituents include, among others, $C_{1-4}$ alkyl (e.g. methyl, ethyl, propyl, butyl, etc.), halogens (e.g. chlorine, bromine, iodine, etc.), nitro, cyano, hydroxy, $C_{1-4}$ alkoxy (e.g. methoxy, ethoxy, propoxy, butyloxy, isopropoxy, etc.), $C_{1-4}$ alkylthio (e.g. methylthio, ethylthio, propylthio, isopropylthio, butylthio, etc.), amino, mono- or di-$C_{1-4}$ alkylamino (e.g. methylamino, ethylamino, propylamino, dimethylamino, diethylamino, etc.), 5- to 8-membered cycloamino (e.g. pyrrolidino, piperidino, hexamethyleneimino, morpholino, thiomorpholino, piperazinyl, imidazolinyl, etc.), $C_{1-4}$ alkylcarbonylamino (e.g. acetylamimo, propionylamino, butyrylamino, etc.), $C_{1-4}$ alkylsulfonylamino (e.g. methylsulfonylamino, ethylsulfonylamino, propylsulfonylamino, etc.), $C_{1-4}$ alkoxycarbonyl (e.g. methoxycarbonyl, ethoxycarbonyl, propoxycarbonyl, isobutoxycarbonyl, etc.), hydroxycarbonyl, $C_{1-4}$ alkylcarbonyl (e.g. methylcarbonyl, ethylcarbonyl, butylcarbonyl, cyclohexylcarbonyl, etc.), carbamoyl, mono-or di-$C_{1-4}$ alkylcarbamoyl (e.g. methylcarbamoyl, ethylcarbamoyl, propylcarbamoyl, butylcarbamoyl, diethylcarbamoyl, dibutylcarbamoyl, etc.) and $C_{1-4}$ alkylsulfonyl (e.g. methylsulfonyl, ethylsulfonyl, propylsulfonyl, etc.) clopentylsulfonyl, cyclohexylsulfonyl, as well as phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl $C_{1-4}$ alkylsulfinyl, phenyl-$C_{1-4}$ alkylsulfonylamino and phenylsulfonylamino, each of which may have 1 to 4 substituents. Here, the substituents on the phenyl or naphthyl ring include, among others, $C_{1-4}$ alkyl (e.g. methyl, ethyl, propyl, butyl, isopropyl, etc., $C_{1-4}$ alkoxy (e.g. methoxy, ethoxy, n-propoxy, i-propoxy, n-butoxy, etc.), halogens (e.g. chlorine, bromine, iodine, etc.), hydroxy, benzoxy, amino, mono- or di-$C_{1-4}$ alkylamino (e.g. methylamino, dimethylamino, etc.), nitro, $C_{1-4}$ alkoxycarbonyl and so on. Preferably, ring B has 1 to 3 substituents (which may be the same or different) selected from the above-mentioned various substituent groups.

Ring A may be a carbocycle or a heterocycle containing 1 to 2 hetero-atoms selected from among O and S and may be saturated or unsaturated.

The substituent groups of ring A include, among others, hydroxy, oxo, lower alkoxycarbonyl, and aromatic groups which may be substituted. Among such lower alkoxycarbonyl groups re $C_{1-4}$ alkoxycarbonyl groups (e.g. methoxycarbonyl, ethoxycarbonyl, n-propoxycarbonyl, n-butoxycarbonyl, t-butoxycarbonyl, etc.).

The "aromatic group" and its "substituents" for the "aromatic group which may be substituted", which is a substituent on ring A, respectively include the aromatic groups and substituents mentioned hereinbefore as examples of the "aromatic group which may be substituted" for $R^2$ and $R^3$.

Preferred species of the compound of the formula (I) include the following.

$R^1$ preferably means methyl, ethyl or isopropyl, and, more desirably, means ethyl.

$R^2$ is preferably an unsubstituted phenyl or naphthyl group or a phenyl or naphthyl group substituted by 1 or 2 alkoxy groups such as methoxy and ethoxy. More specifically, $R^2$ preferably means phenyl, 2-methoxyphenyl, 3-methoxyphenyl, 2,3-dimethoxyphenyl or naphthyl.

$R^3$ is preferably a hydrogen atom.

The symbol n preferably stands for 3, 4 or 5.

Preferred examples of the group

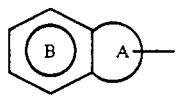

include groups of the formulas:

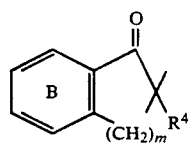

wherein m stands for 1, 2 or 3; $R^4$ means a hydrogen atom, a lower alkoxycarbonyl group or an aromatic group which may be substituted.

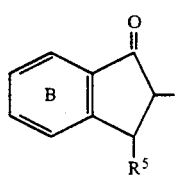

wherein $R^5$ means an aromatic group which may be substituted.

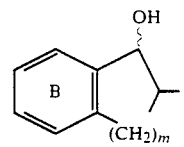

wherein all symbols are respectively as defined above.

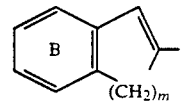

wherein all symbols are respectively as defined above.

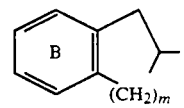

wherein all symbols are respectively as defined above.

The aromatic group which may be substituted, as represented by $R^4$ and $R^5$, is the same as the aromatic group which may be substituted as mentioned above with reference to the substituent group of ring A, and the lower alkoxycarbonyl, as represented by $R^4$, is the same as the lower alkoxycarbonyl as mentioned above with reference to the substituent group of ring A.

Preferred substituents for ring B, among those mentioned hereinbefore, are $C_{1-4}$ alkoxy, nitro, cyano, halogens, $C_{1-4}$ alkylcarbonylamino, $C_{1-4}$ alkylsulfonyl, piperidino, pyrrolidino and so on.

The compound (I) of the present invention may be provided in the form of an acid addition salt, particularly a physiologically acceptable acid addition salt. Examples of such salt include salts with inorganic acids (e.g. hydrochloric acid, nitric acid, phosphoric acid, hydrobromic acid, sulfuric acid, etc.) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid, etc.).

When compound (I) has an acidic group, such as —COOH, it may be provided in the form of salt with an inorganic base, such as sodium, potassium, calcium, magnesium, ammonia, etc., or with an organic base such as triethylamine and so on.

The process for production of compound (I) according to the present invention is described below.

It should be understood that the term 'compound (I)' as used in the following description means not only the compound (I) as such but also its salt.

Compound (I) can be produced by reacting, for example, a compound of formula (II)

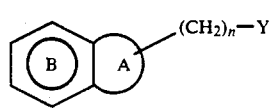 (II)

wherein Y means a leaving group such as a halogen atom or an alkyl- or aryl-sulfonyloxy group and other symbols are respectively as defined hereinbefore with, for example, a compound of formula (III)

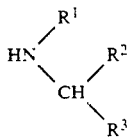

wherein all symbols are respectively as defined hereinbefore or a salt thereof.

The alkyl moiety of said alkyl- or aryl-sulfonyl group as represented by Y includes, among others, $C_{1-4}$ alkyl groups such as methyl, ethyl, propyl, etc. and the aryl moiety includes, among others, phenyl and substituted phenyl such as p-methylphenyl and so on. The salt of compound (III) includes various acid addition salts such as those mentioned for the salt of compound (I). This reaction is carried out using a solvent or in the absence of a solvent. The reaction can also be carried out in the presence of a base or without using a base.

The base mentioned just above can be selected from among inorganic bases such as sodium carbonate, potassium carbonate, lithium carbonate, sodium hydroxide, potassium hydroxide, sodium methoxide, sodium ethoxide, sodium hydride, etc. and organic bases such as pyridine, 4-dimethylaminopyridine, triethylamine and so on. The solvent, if used, can be selected from among various solvents which do not interfere with the reaction, e.g. lower alcohols such as methanol, ethanol, propanol, isopropyl alcohol, n-butanol, t-butanol, etc., various ethers such as dioxane, ether, tetrahydrofuran, etc., aromatic hydrocarbons such as toluene, benzene, xylene, etc., various amides such as dimethylformamide, dimethylacetamide, hexamethylphosphonotriamide, etc., and various esters such as ethyl acetate, butyl acetate, and so on. This reaction can be conducted under cooling (about 0° to 10° C.), at room temperature (about 10° to 40° C.) or under heating (about 40° to 120° C.) and the reaction time is generally 10 minutes to 48 hours and preferably about 2 to 16 hours. The preferred proportion of compound (III) is generally 3 to 5.0 moles to each mole of compound (II). The amount of the base, if used, is generally at least equimolar and preferably 1.1 to 5 equivalents based on compound (III). If desired, this reaction can be conducted in the presence of an iodide such as sodim iodide, potassium iodide, lithium iodide or the like. The amount of such iodide, if used, is generally 1 to 5 equivalents and preferably 1.1 to 1.5 equivalents relative to compound (II).

The above compound of the formula (II) can be prepared by any of the known processes, for example the processes described in Journal of Organic Chemistry 33, 2457 (1968) and 39, 2637 (1974), or any process analogous thereto.

Using the thus-obtained specific compound (I) as a starting material, other species of compound (I) can be provided.

For example, of compound (I), a species having a group of the formula

ring A be produced by subjecting a compound a lower alkoxycarbonyl group alpha to the group

to hydrolysis and, then, to decarboxylation, by the known procedures, for example the process described in Journal of Organic Chemistry 33, 2457 (1968) or a process analogous thereto.

To mention a specific example, a species of compound (I) which has the formula

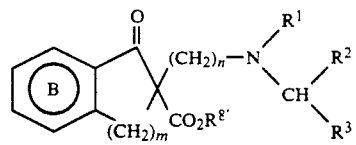

wherein $R^{6'}$ means a lower alkyl group and all other symbols are respectively as defined hereinbefore is hydrolyzed and, then, decarboxylated to give a species of compound (I) which can be written as

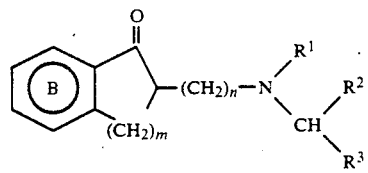

wherein all symbols are respectively as defined hereinbefore.

Of compound (I), a species having a group of the formula

or —$CH_2$— on ring A can be produced by reducing a species in which the corresponding group is

This reduction reaction can be carried out by a per se known procedure, for example, by using a metal hydride complex compound such as lithium aluminum hydride, sodium borohydride or the like.

To give a specific example, a species of compound (I) having the formula

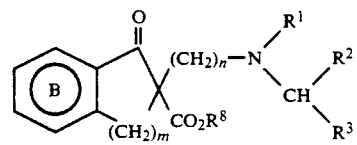

wherein $R^6$ means a hydrogen atom, a lower alkoxycarbonyl group or an aromatic group which may be substituted and all other symbols are respectively as defined hereinbefore or a salt thereof is reduced to a species of compound (I) which may be written as

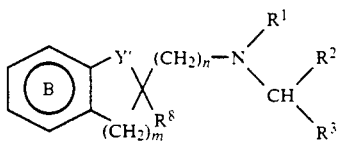

wherein m, n R¹, R², R³ and R⁴ are respectively as defined hereinbefore and Y' means

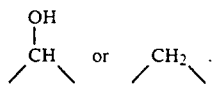

Here, the "lower alkoxycarbonyl group" and "aromatic group which may be substituted" for R₆ are those mentioned hereinbefore for the substituents on ring A.

Of compound (I), a species containing a group of the formula >CH=C< on ring A can be produced by subjecting a species in which the corresponding group on ring A is a group of the formula

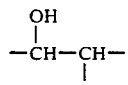

to a dehydration reaction in the presence of an acid. The acid may be an inorganic acid, such as hydrochloric acid, sulfuric acid, etc., or an organic acid, such as p-toluenesulfonic acid and so on. This dehydration reaction can be carried out by the per se known method.

To mention a specific example, a species of the formula

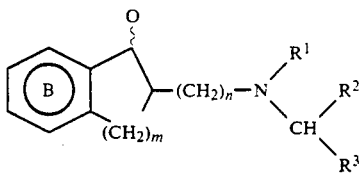

wherein all symbols are respectively as defined hereinbefore or a salt thereof is dehydrated to give a species of compound (I) which can be written as

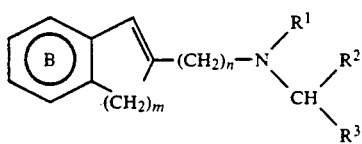

wherein all symbols are respectively as defined hereinbefore.

A compound containing an amino group, a mono- or di-$C_{1-4}$ alkylamino group or a 5- to 8-membered cycloamino group on benzene ring B can be produced, also, by reacting a compound having an activated fluorine atom on benzene ring B, for example a compound of the formula

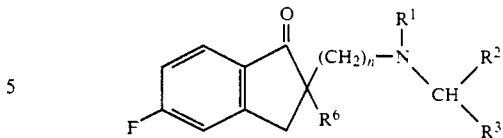

wherein all symbols are respectively as defined hereinbefore with the corresponding amine by a per se known procedure.

The compound (I) can be produced by other known processes or processes analogous thereto as well.

The compounds (I) of the present invention act on the central nervous system of mammals, where they exert potent anticholinesterase activity to show an excellent antiamnesic action against various types of induced amnesia in man and animals (e.g. mice).

Compared with physostigmine, the compound (I) of the invention is characterized by a distinct separation of its action on central nerves from that on peripheral nerves, scarcely producing peripheral nervous symptoms such as spasm, salivation and diarrhea, if any, at antiamnesically effective doses and being long-acting and low in toxicity. Moreover, the compound produces remarkable effects on oral administration.

Therefore, the compound of the invention is useful as a brain function ameliorating agent for mammals including man.

The diseases in which the compound of the invention may be indicated are, for example, senile dementia, Alzheimer's disease, Huntington's chorea, hyperkinesia and mania. The compound can be used in the prevention or treatment of these diseases The compound of the present invention can be administered, orally or parenterally, to mammalian animals inclusive of man in various dosage forms such as tablets, granules, capsules, injections, suppositories and so on. While the dosage depends on such factors as the type and symptoms of the disease to be treated, the daily oral dosage per adult human is about 0.001 to 100 mg, preferably about 0.01 to 30 mg, and more desirably about 0.3 to 10 mg.

The compound according to the present invention acts on the central nervous system of mammals and exerts potent anticholinesterase activity. Therefore, it can be used in the prevention and treatment of various diseases such as senile dementia, Alzheimer's disease, Huntington's chorea and so on. Thus, the compound is a useful drug.

The following working, reference, preparation and test examples are intended to illustrate the invention in further detail and should by no means be construed as defining the scope of the invention.

In the working and reference examples which appear hereinafter, elution procedures in column chromatography were carried out under monitoring by thin-layer chromatography (TLC) unless otherwise indicated. In TLC monitoring, Merck's 60 $F_{254}$ was used as the TLC plate, the eluent for column chromatography as the developing solvent, and an UV detector as the spot detection means. For identification of the fractions rich in each objective compound, the detection method comprising spraying the TLC plate with a 48% HBr solution, hydrolyzing it by heating, spraying a ninhydrin reagent and reheating to detect a change of color to red-reddish purple was used in conjunction Furthermore, unless otherwise indicated, Merck's Kieselgel 60

(70–230 mesh) was used as silica gel for column chromatography.

It should also be understood that the terms "atmospheric temperature" and "room temperature" are both used to mean a temperature within the range of about 5° C. to 40° C. and the terms "atmospheric pressure" are used to mean a pressure in the neighborhood of one atmosphere.

All percents (%) are by weight unless otherwise indicated.

REFERENCE EXAMPLE 1

Ethyl 2-(5-bromopentyl)-5,6-dimethoxy-1-indanone-2-carboxylate

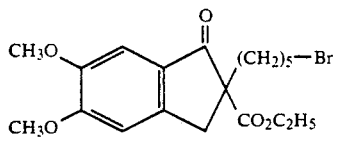

To a solution of ethyl 5,6-dimethoxy-1-indanone-2-carboxylate (1.0 g) in dimethylformamide (10 ml) was added sodium hydride (0.11 g) and the mixture was stirred at room temperature for 30 minutes. Then, 1,5-dibromopentane (1.8 g) was added and the mixture was further stirred for 2 hours. The reaction was then stopped by adding water and the product was extracted into dichloromethane. The extract was washed with water and dried over anhydrous sodium sulfate and the solvent was distilled off under reduced pressure. The oily residue was subjected to silica gel column chromatography (eluent: dichloromethane - ethyl acetate =20:1, v/v) and the fractions rich in the title compound were pooled. Finally, the solvent was distilled off to give 1.1 g of colorless crystals melting at 85°–87° C.

Elemental analysis, $C_{18}H_{25}BrO_5$ Calcd.: C, 55.22; H, 6.10 Found : C, 55.31; H, 6.05

REFERENCE EXAMPLE 2

In substantially the same manner as Reference Example 1, the compounds shown in Table 1 were synthesized.

TABLE 1

| Compound No. | B–A–(CH$_2$)$_n$–Br structure | n | Melting point (°C.) | Molecular formula | Elemental analysis Calcd. (Found) C | H |
|---|---|---|---|---|---|---|
| 1 | CH$_3$O, CH$_3$O – indanone – CO$_2$C$_2$H$_5$ | 4 | 94–96 | $C_{18}H_{23}BrO_5$ | 54.15 (54.02 | 5.81 5.73) |
| 2 | CH$_3$O, CH$_3$O – indanone – CO$_2$C$_2$H$_5$ | 3 | 77–78 | $C_{17}H_{21}BrO_5$ | 53.00 (52.83 | 5.49 5.41) |
| 3 | CH$_3$O, CH$_3$O – indanone – Ph | 5 | Oil | $C_{22}H_{25}BrO_3$ | 63.32 (63.09 | 6.04 5.82) |
| 4 | CH$_3$O, CH$_3$O – indanone – CO$_2$C$_2$H$_5$ | 2 | 93–94 | $C_{16}H_{19}BrO_5$ | 51.77 (51.55 | 5.16 5.24) |
| 5 | F – indanone – CO$_2$C$_2$H$_5$ | 4 | Oil | $C_{16}H_{18}BrFO_3$ | 53.80 (53.74 | 5.08 4.97) |

EXAMPLE 1

Ethyl 5,6-dimethyl-2-[5-[N-ethyl-N-[(2-methoxyphenyl)methyl]amino]pentyl]-1-indanone-2-carboxylate

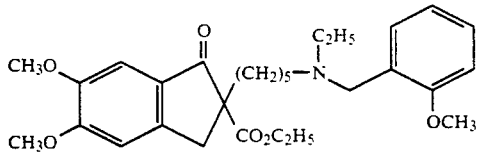

A solution of the ethyl 2-(5-bromopentyl)-5,6-dimethoxy-1-indanone-2-carboxylate prepared in Reference Example 1 (0.16 g) and N-ethyl-N-[(2-methoxyphenyl)-methyl]amine (0.13 g) in toluene (5 ml) was refluxed for 16 hours and the solvent was then distilled off. The remaining oil was subjected to column chromatography (eluent: ethyl acetate - methanol =20:1, v/v) and the fractions rich in the title compound were pooled. Finally, the solvent was distilled off under reduced pressure to give 0.15 g of a colorless oil.

Elemental analysis, $C_{29}H_{39}NO_6$ Calcd.: C, 70.00; H, 7.90; N, 2.81 Found: C, 69.85; H, 7.91; N, 2.68

EXAMPLE 2

5,6-Dimethoxy-2-[5-[N-ethyl-N-[(2-methoxyphenyl)-methyl]amino]pentyl]-1-indanone hydrochloride

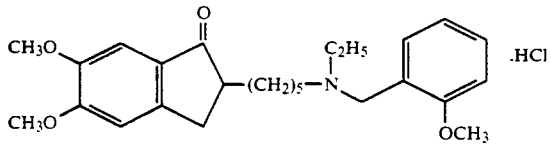

A solution of the ethyl 2-(5-borompentyl)-5,6-dimethoxy-1-indanone-2-carboxylate prepared in Reference Example 1 (0.7 g) and N-ethyl-N-[(2-methoxyphenyl)-methyl] amine (0.56 g) in toluene (15 ml) was refluxed for 12 hours and the solvent was then distilled off under reduced pressure. The remaining oil was dissolved in ethanol (10 ml) and after addition of a solution of potassium hydroxide (0.63 g) in water (2 ml), the mixture was refluxed for 6 hours. The solvent was then distilled off under reduced pressure and the residue was diluted with water (50 ml). The product was extracted into dichloromethane and the extract was washed with water and dried over anhydrous sodium sulfate. The solvent was then distilled off under reduced pressure and the remaining oil was subjected to column chromatography (eluent: ethyl acetate - methanol=20:1, v/v). The fractions rich in the desired compound were pooled and the solvent was distilled off. To the residue was added 0.56 ml of 3N ethanolic hydrochloric acid and the solvent was then distilled off to give 0.58 g of a hygroscopic amorphous powder.

Elemental analysis, $C_{26}H_{35}NO_4 \cdot HCl$ Calcd.: C, 67.59; H, 7.85; N, 3.03 Found: C, 67.31; H, 7.66; N, 2.81

EXAMPLE 3

The compounds shown in Table 2 were synthesized in substantially the same manner as Example 2.

TABLE 2

| Compound No. | B-A | n | R | Melting point (°C.) | Molecular formula | Elemental analysis Calcd. (Found) C | H | N |
|---|---|---|---|---|---|---|---|---|
| 1 | 5,6-dimethoxy-indanone | 5 | phenyl | Amorphous | $C_{25}H_{33}NO_3 \cdot HCl$ | 69.51 (69.28 | 7.93 7.76 | 3.24 3.30) |
| 2 | 5,6-dimethoxy-indanone | 4 | 2-methoxyphenyl | Amorphous | $C_{25}H_{33}NO_4 \cdot HCl$ | 67.03 (66.87 | 7.65 7.44 | 3.13 2.98) |
| 3 | 5,6-dimethoxy-indanone | 4 | phenyl | Amorphous | $C_{24}H_{31}NO_3 \cdot HCl$ | 68.97 (68.79 | 7.72 7.55 | 3.35 3.09) |

TABLE 2-continued

General structure: B-A-(CH$_2$)$_n$-N(C$_2$H$_5$)(CH$_2$-R)

| Compound No. | B-A structure | n | R | Melting point (°C.) | Molecular formula | Elemental analysis Calcd. (Found) C | H | N |
|---|---|---|---|---|---|---|---|---|
| 4 | 5,6-dimethoxy-indan-1-one | 3 | 2-methoxyphenyl | Amorphous | C$_{24}$H$_{31}$NO$_4$·HCl | 66.42 (66.15 | 7.43 7.03 | 3.23 3.04) |
| 5 | 5,6-dimethoxy-indan-1-one | 2 | 2-methoxyphenyl | Amorphous | C$_{23}$H$_{29}$NO$_4$·HCl | 65.78 (65.69 | 7.20 7.04 | 3.34 3.29) |
| 6 | 5,6-dimethoxy-indan-1-one | 3 | 2-methoxyphenyl | 139–141 | C$_{24}$H$_{31}$NO$_4$·C$_4$H$_4$O$_4$ (fumarate) | 65.48 (65.40 | 6.87 6.69 | 2.73 2.66) |
| 7 | 5,6-dimethoxy-indan-1-one | 4 | 2-methoxyphenyl | 144–146 | C$_{25}$H$_{33}$NO$_4$·C$_4$H$_4$O$_4$ (fumarate) | 66.02 (65.95 | 7.07 6.99 | 2.66 2.60) |
| 8 | 5,6-dimethoxy-indan-1-one | 4 | 3-methoxyphenyl | 96–98 | C$_{25}$H$_{33}$NO$_4$·C$_4$H$_4$O$_4$ (fumarate) | 66.02 (65.85 | 7.07 7.02 | 2.66 2.58) |
| 9 | 4,5,6-trimethoxy-indan-1-one | 4 | 2-methoxyphenyl | 94–96 | C$_{28}$H$_{35}$NO$_5$·C$_4$H$_4$O$_4$ (fumarate) | 64.62 (64.51 | 7.05 6.94 | 2.51 2.37) |
| 10 | 5-methoxy-indan-1-one | 4 | 2-methoxyphenyl | 113–115 | C$_{24}$H$_{31}$NO$_3$·C$_4$H$_4$O$_4$ (fumarate) | 67.59 (67.44 | 7.09 6.92 | 2.82 2.78) |
| 11 | 5,6-methylenedioxy-indan-1-one | 4 | 2-methoxyphenyl | 137–139 | C$_{24}$H$_{29}$NO$_4$·C$_4$H$_4$O$_4$ (fumarate) | 65.74 (65.59 | 6.50 6.41 | 2.74 2.63) |
| 12 | 6-methoxy-tetralin-1-one | 5 | 2-methoxyphenyl | Amorphous | C$_{28}$H$_{35}$NO$_3$·HCl | 70.02 (69.88 | 8.14 7.96 | 3.14 3.01) |

TABLE 2-continued
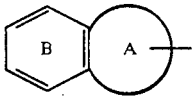
| Compound No. | 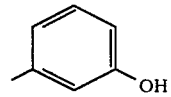 | n | R | Melting point (°C.) | Molecular formula | Elemental analysis Calcd. (Found) C | H | N |
|---|---|---|---|---|---|---|---|---|
| 13 | 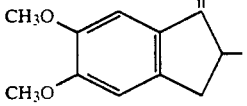 | 3 | 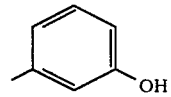 | Amorphous | C$_{23}$H$_{29}$NO$_4$.HCl | 65.78 (65.72 | 7.20 7.02 | 3.34 3.19) |
| 14 | 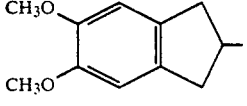 | 4 | 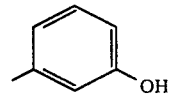 | Amorphous | C$_{24}$H$_{31}$NO$_4$.HCl | 66.42 (66.36 | 7.43 7.29 | 3.23 3.07) |
| 15 | 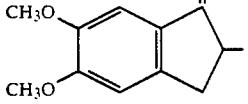 | 6 | 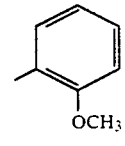 | Amorphous | C$_{27}$H$_{37}$NO$_4$.HCl | 68.12 (68.10 | 8.05 8.00 | 2.94 2.82) |
| 16 | 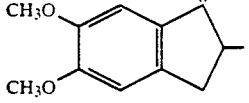 | 4 | 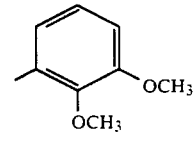 | Amorphous | C$_{28}$H$_{35}$NO$_5$.HCl | 65.33 (65.09 | 7.59 7.41 | 2.93 2.76) |
| 17 | 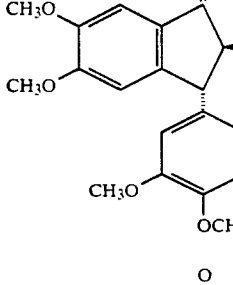 | 4 | 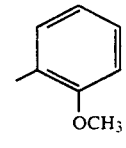 | Amorphous | C$_{33}$H$_{41}$NO$_8$.HCl | 67.85 (67.71 | 7.25 7.05 | 2.40 2.28) |
| 18 | 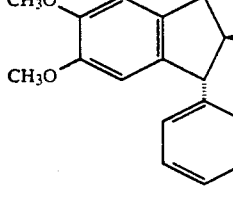 | 3 | 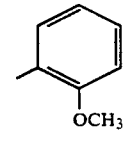 | Amorphous | C$_{30}$H$_{35}$NO$_4$.HCl | 70.64 (70.51 | 7.11 6.94 | 2.75 2.59) |
| 19 | 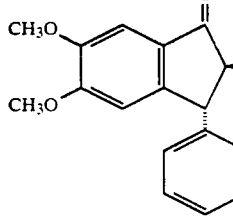 | 4 | 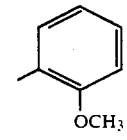 | Amorphous | C$_{31}$H$_{37}$NO$_4$.HCl | 71.04 (70.83 | 7.31 7.23 | 2.67 2.50) |

TABLE 2-continued

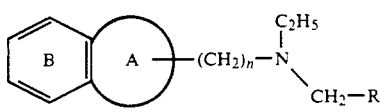

| Compound No. | 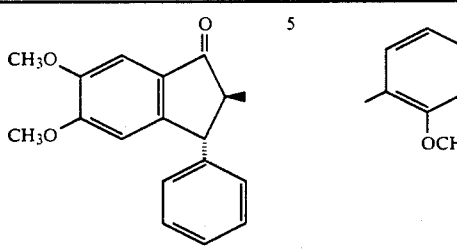 | n | R | Melting point (°C.) | Molecular formula | Elemental analysis Calcd. (Found) C | H | N |
|---|---|---|---|---|---|---|---|---|
| 20 | 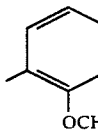 | 5 | 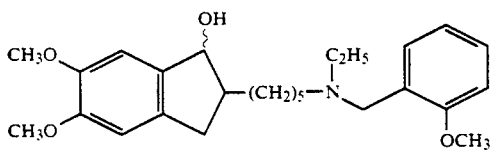 | Amorphous | $C_{32}H_{38}NO_4 \cdot HCl$ | 71.42 (71.31 | 7.49 7.39 | 2.60 2.47 |

EXAMPLE 4

1,2-Dihydro-5,6-dimethoxy-2-[5-[N-ethyl-N-[(2-methoxyphenyl)methyl]amino]pentyl]-1-hydroxyindene

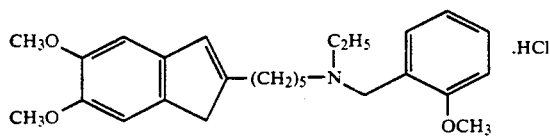

To a solution of the 5,6-dimethoxy-2-[5-[N-ethyl-N-[(2-methoxyphenyl)methyl]amino]pentyl]-1-indanone hydrochloride (0.75 g) in methanol (10 ml) was gradually added sodium borohydride (0.3 g) and the mixture was stirred at room temperature for 6 hours. The excess sodium borohydride was then decomposed by addition of water and the solvent was distilled off under reduced pressure. The product was extracted into dichloromethane and washed with water. The dichloromethane layer was dried over anhydrous sodium sulfate and the solvent was distilled off to give 0.63 g of a colorless oil.

Elemental analysis, $C_{26}H_{37}NO_4$ Calcd.: C, 73.04; H, 8.72; N, 3.28 Found : C, 72.91; H, 8.56; N, 3.20

EXAMPLE 5

5,6-Dimethoxy-2-[5-[N-ethyl-N-[(2-methoxyphenyl)methyl]amino]pentyl]indene hydrochloride

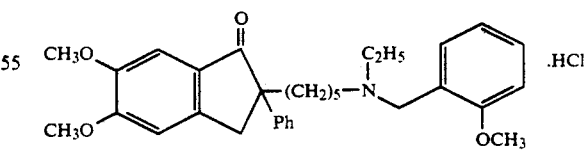

To a solution of the 1,2-dihydro-5,6-dimethoxy-2-[5-[N-ethyl-N-[(2-methoxyphenyl)methyl]amino]pentyl]-1-hydroxyindene (0.4 g) in toluene-ethanol (10 ml/2 ml) was added concentrated sulfuric acid (1 drop) and the mixture was heated at 100° C with stirring for 30 minutes. The solvent was then distilled off and the residue was diluted with 5% aqueous sodium hydroxide solution (10 ml) and extracted with dichloromethane. The extract was washed with water and dried over anhydrous sodium sulfate and the solvent was distilled off. To the residue was added 3N-ethanolic hydrochloric acid (0.3 ml) and the solvent was distilled off to give 0.39 g of a hygroscopic amorphous powder.

Elemental analysis, $C_{26}H_{35}NO_3 \cdot HCl$ Calcd.: C, 70.02; H, 8.14; N, 3.14 Found : C, 69.94; H, 8.01; N, 3.04

EXAMPLE 6

5,6-Dimethoxy-2-[5-[N-ethyl-N-[(2-methoxyphenyl)methyl]amino]pentyl]-2-phenyl-1-indanone hydrochloride A colorless amorphous powder was obtained in substantially the same manner as Example 1. Elemental analysis, $C_{32}H_{29}NO_4 \cdot HCl$ Calcd.: C, 71.42; H, 7.49; N, 2.60 Found : C, 71.33; H, 7.41; N, 2.46

EXAMPLE 7

2-[4-[N-Ethyl-N-(phenylmethyl)amino]butyl]-5-pyrrolidino-1-indanone fumarate

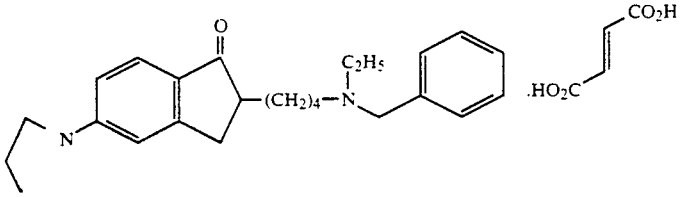

A solution of the ethyl 2-(4-bromobutyl)-5-fluoro-1-indanone-2-carboxylate (Compound No. 5) prepared in Reference Example 2 (1.5 g) and N-ethyl-N-(phenylmethyl)amine (1.14 g) in toluene (15 ml) was refluxed for 16 hours, at the end of which time the solvent was distilled off under reduced pressure The oily residue was subjected to column chromatography (eluent: ethyl acetate) and the fractions rich in ethyl 2-[4-[N-ethyl-N-(phenylmethyl)amino]butyl]-5-fluoro-1-indanone-2-carboxylate were pooled. The solvent was then distilled off under reduced pressure to recover 1.05 g of a colorless oil. The oily product (1.0 g) was reacted with pyrrolidine (3 ml) in a sealed tube at 100° C for 4 hours. After the pyrrolidine was distilled off under reduced pressure, ethanol (10 ml), water (2 ml) and potassium hydroxide (1 g) were added to the residue and the mixture was refluxed for 2 hours. The solvent was then distilled off under reduced pressure and the product was extracted into dichloromethane. The extract was washed with water and dried over anhydrous sodium sulfate and the solvent was distilled off under reduced pressure. The oil residue was subjected to column chromatography (eluent: ethyl acetate) and the fractions rich in the desired compound were pooled and the solvent was distilled off under reduced pressure to give 0.7 g of a colorless oil. This oil (0.7 g) and fumaric acid (0.21 g) were dissolved in methanol to give a homogeneous solution and the solvent was then distilled off under reduced pressure to give 0.9 g of a colorless amorphous powder.

Elemental analysis, $C_{26}H_{34}N_2O \cdot C_4H_4O_4$ Calcd.: C, 71.12; H, 7.56; N, 5.53 Found : C, 70.03; H, 7.41; N, 5.51

EXAMPLE 8

2-[4-[N-Ethyl-N-[(2-methoxyphenyl)methyl]amino]butyl]-5-pyrrolidino-1-indanone fumarate

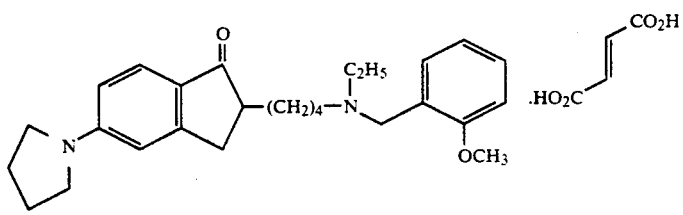

A colorless amorphous powder was prepared in substantially the same manner as Example 7.

Elemental analysis, $C_{27}H_{36}N_2O_2 \cdot C_4H_4O_4$ Calcd.: C, 69.38; H, 7.51; N, 5.22 Found : C, 69.24; H, 7.45; N, 5.01

PREPARATION EXAMPLE 1

| | | |
|---|---|---|
| (1) | 5,6-Dimethoxy-2-[5-[N-ethyl-N-[(2-methoxyphenyl)methyl]amino]pentyl]-1-indanone hydrochloride (the compound synthesized in Example 2) | 1 g |
| (2) | Lactose | 197 g |
| (3) | Corn starch | 50 g |
| (4) | Magnesium stearate | 2 g |

(1), (2) and 20 g of corn starch were mixed and granulated with a paste prepared from 15 g of corn starch and 25 ml of water. To this granulation were added 15 g of corn starch and (4) and the mixture was molded with a compression tablet molding machine to give 2000 tablets each measuring 3 mm in diameter and containing 0.5 mg of (1).

PREPARATION EXAMPLE 2

| | | |
|---|---|---|
| (1) | 5,6-Dimethoxy-2-[5-[N-ethyl-N-[(2-methoxyphenyl)methyl]amino]pentyl]-1-indanone hydrochloride (the compound synthesized in Example 2) | 2 g |
| (2) | Lactose | 196 g |
| (3) | Corn starch | 50 g |
| (4) | Magnesium stearate | 2 g |

(1), (2) and 20 g of corn starch were mixed and granulated with a paste prepared from 15 g of corn starch and 25 ml of water. To this granulation were added 15 g of corn starch and (4) and the mixture was molded with a compression tablet molding machine to give 2,000 tablets each measuring 5 mm in diameter and containing 1 mg of (1).

Test Example 1

The anticholinesterase activity of the compound of the invention was evaluated using (acetyl-[$^3$H])-acetylcholine. The $S_1$ fraction of a cerebral cortex homogenate from male Wistar rats was used as the cholinesterase source, (acetyl-[$^3$H])-acetylcholine as the substrate and the test compound of the invention as the test substance. The incubation was carried out for 30 minutes and after the reaction was terminated, the system was shaken with a toluene scintillator to thereby transfer [$^3$H]-acetic acid into the toluene layer. The radioactivity in the toluene layer was then measured with a liquid scintillation counter to estimate the anticholinesterase activity of the test compound.

The anticholinesterase activity of the test compound was expressed in 50% inhibitory concentration (IC$_{50}$). As a control, the anticholinesterase activity of physostigmine was also estimated in the same manner. The results are set forth in Table 3.

TABLE 3

| Compound (Example No.) | Anticholinesterase activity, IC$_{50}$ ($\mu$M) |
| --- | --- |
| 2 | 0.0060 |
| 3-1 | 0.12 |
| 3-2 | 0.020 |
| 3-3 | 0.076 |
| 3-4 | 0.011 |
| 3-5 | 0.68 |
| 3-6 | 0.014 |
| 3-7 | 0.027 |
| 3-8 | 0.11 |
| 3-9 | 0.090 |
| 3-10 | 0.11 |
| 3-11 | 0.17 |
| 3-12 | 0.13 |
| 3-13 | 0.21 |
| 3-14 | 0.63 |
| 3-15 | 0.10 |
| 4 | 0.16 |
| 5 | 0.60 |
| 7 | 0.143 |
| 8 | 0.081 |
| Physostigmine | 0.22 |

For example, compound 3-1 means the compound No. 1 of Example 3.

It is apparent from the above results that the compound of the present invention has excellent anticholinesterase activity.

We claim:

1. An aralkylamine compound of the formula

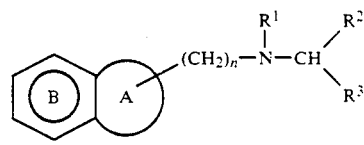

wherein $R^1$ means a hydrogen atom or a lower alkyl group; $R^2$ means a phenyl or naphthyl optionally substituted with one or two C$_{1-4}$ alkoxy groups; $R^3$ means a hydrogen atom; n means an integer of 3, 4 or 5; ring A means a five-membered carbocyclic group optionally substituted by (i) hydroxyl, (ii) oxo or (iii) a phenyl group optionally substituted with one or two C$_{1-2}$ alkoxy groups; and ring B means a benzene ring optionally substituted with one to three substituents selected from the group consisting of halogen, nitro, C$_{1-4}$ alkoxy, and C$_{1-4}$ alkylsulfonyl, or a physiologically acceptable salt thereof.

2. An aralkylamine compound of claim 1 wherein $R^1$ is ethyl, $R^3$ is a hydrogen atom and $R^2$ is a phenyl or naphthyl which may be substituted by one to two C$_{1-2}$ alkoxy group(s).

3. A compound which is 5,6-dimethoxy-2-[4-[N-ethyl-N-[(2-methoxyphenyl)methyl]amino]butyl]-1-indanone fumarate.

4. A pharmaceutical composition containing an effective cholinesterase inhibiting amount of a compound of claim 1 and an inert pharmaceutical carrier.

5. A compound which is 5,6-dimethoxy-2-[4-[N-ethyl-N-[(2-methoxyphenyl)methyl]-amino]propyl-1-indanone fumarate.

6. A method of inhibiting cholinesterase in a patient which comprises administering to a mammal a cholinesterase inhibiting amount of a compound of claim 1.

7. A method of inhibiting cholinesterase in a patient which comprises administering to a mammal a cholinesterase inhibiting amount of 5,6-dimethoxy-2-[4-[N-ethyl-N-[(2-methoxyphenyl(methyl]-amino]propyl-1-indanone fumarate.

* * * * *